(12) United States Patent
Terasawa et al.

(10) Patent No.: US 10,295,477 B2
(45) Date of Patent: May 21, 2019

(54) METHODS FOR DEFECT INSPECTION, SORTING, AND MANUFACTURING PHOTOMASK BLANK

(71) Applicant: Shin-Etsu Chemical Co., Ltd., Tokyo (JP)

(72) Inventors: Tsuneo Terasawa, Echizen (JP); Hiroshi Fukuda, Echizen (JP); Atsushi Yokohata, Echizen (JP); Takahiro Kishita, Joetsu (JP); Daisuke Iwai, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 15/880,158

(22) Filed: Jan. 25, 2018

(65) Prior Publication Data

US 2018/0209916 A1  Jul. 26, 2018

(30) Foreign Application Priority Data

Jan. 26, 2017 (JP) .................. 2017-011779
Dec. 20, 2017 (JP) .................. 2017-243900

(51) Int. Cl.
  *G01N 21/88* (2006.01)
  *G01N 21/956* (2006.01)
  *G03F 1/84* (2012.01)

(52) U.S. Cl.
  CPC ....... *G01N 21/8851* (2013.01); *G01N 21/956* (2013.01); *G03F 1/84* (2013.01);
  (Continued)

(58) Field of Classification Search
  CPC ..... G03F 1/84; G03F 1/50; G03F 1/72; G03F 7/7065; G01N 2021/8874; G01N 2021/95676; G01N 21/8851; G01N 21/956
  (Continued)

(56) References Cited

U.S. PATENT DOCUMENTS 6,617,603 B2  9/2003  Ishiguro et al.
7,379,176 B2  5/2008  Sekine et al.
  (Continued)

FOREIGN PATENT DOCUMENTS

JP  2001-174415 A   6/2001
JP  2002-333313 A  11/2002
  (Continued)

OTHER PUBLICATIONS

Extended European Search Report dated Jun. 1, 2018, in European Patent Application No. 18153551.9.

*Primary Examiner* — Tri T Ton
(74) *Attorney, Agent, or Firm* — Birch, Stewart, Kolasch & Birch, LLP

(57) ABSTRACT

A photomask blank having a thin film on a transparent substrate is inspected for defects by irradiating inspection light to a surface region of the blank, collecting the reflected light from the irradiated region via an inspection optical system to form a magnified image of the region, extracting a feature parameter of light intensity distribution from the magnified image, and identifying the bump/pit shape of the defect based on the feature parameter combined with the structure of the thin film. The defect inspection method is effective for discriminating defects of bump or pit shape in a highly reliable manner. On application of the defect inspection method, photomask blanks having no pinhole defects are available at lower costs and higher yields.

18 Claims, 15 Drawing Sheets

(52) U.S. Cl.
CPC .............. *G01N 2021/8874* (2013.01); *G01N 2021/95676* (2013.01)

(58) Field of Classification Search
USPC .................. 356/237.1–237.6, 239.1–239.8
See application file for complete search history.

(56) References Cited

U.S. PATENT DOCUMENTS

| | | | |
|---|---|---|---|
| 7,630,068 B2 | 12/2009 | Tanaka et al. | |
| 7,911,600 B2 | 3/2011 | Terasawa et al. | |
| 2007/0188743 A1* | 8/2007 | Tanaka ................. | B82Y 10/00 356/237.1 |
| 2016/0116837 A1* | 4/2016 | Terasawa ............. | G01N 21/956 430/5 |
| 2016/0377553 A1* | 12/2016 | Terasawa ............... | G01B 11/24 430/5 |

FOREIGN PATENT DOCUMENTS

| | | |
|---|---|---|
| JP | 2005-265736 A | 9/2005 |
| JP | 2007-219130 A | 8/2007 |
| JP | 2013-19766 A | 1/2013 |

\* cited by examiner

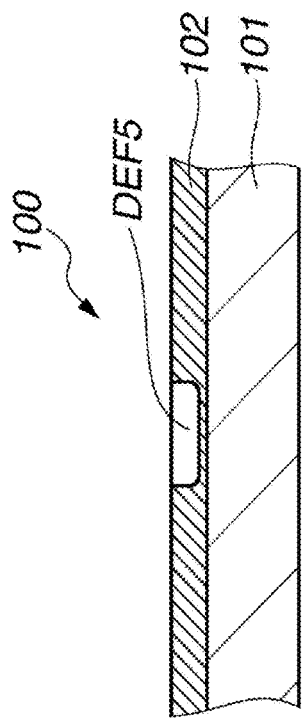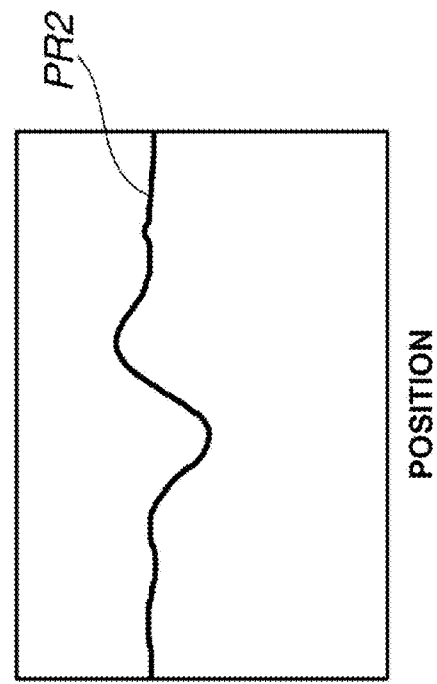
FIG.4A
FIG.4B

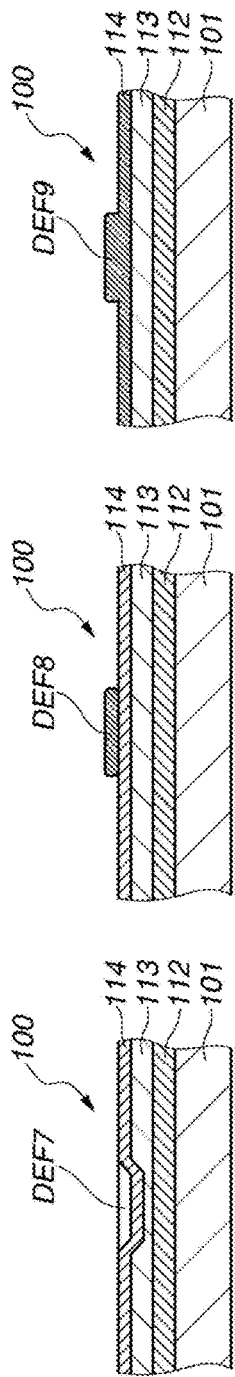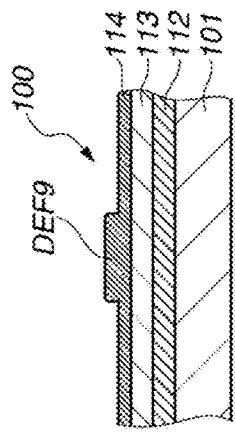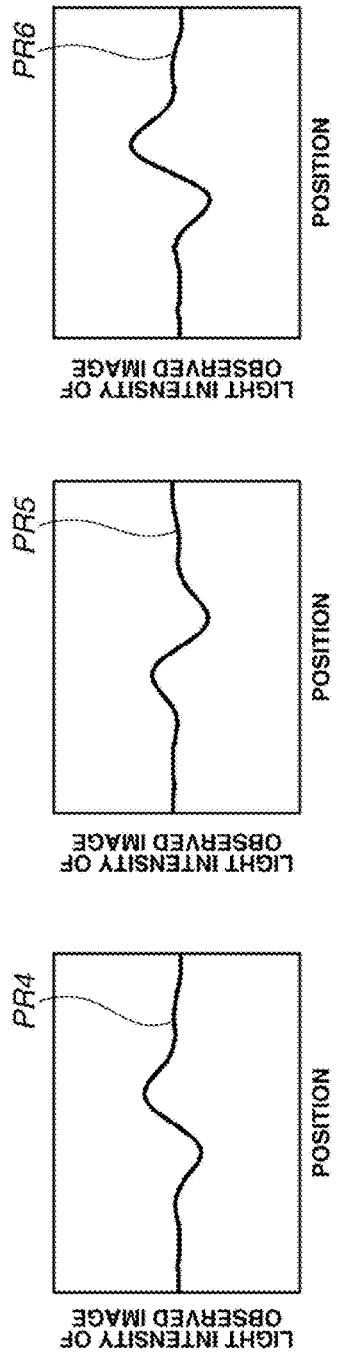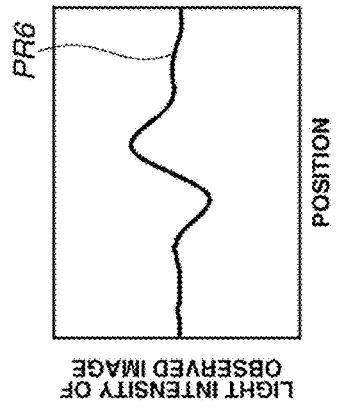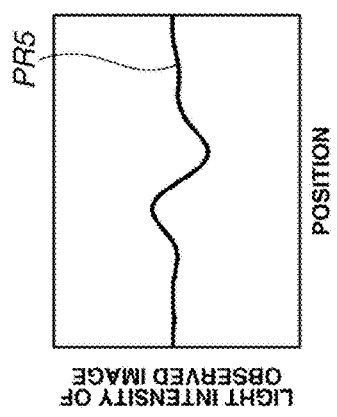

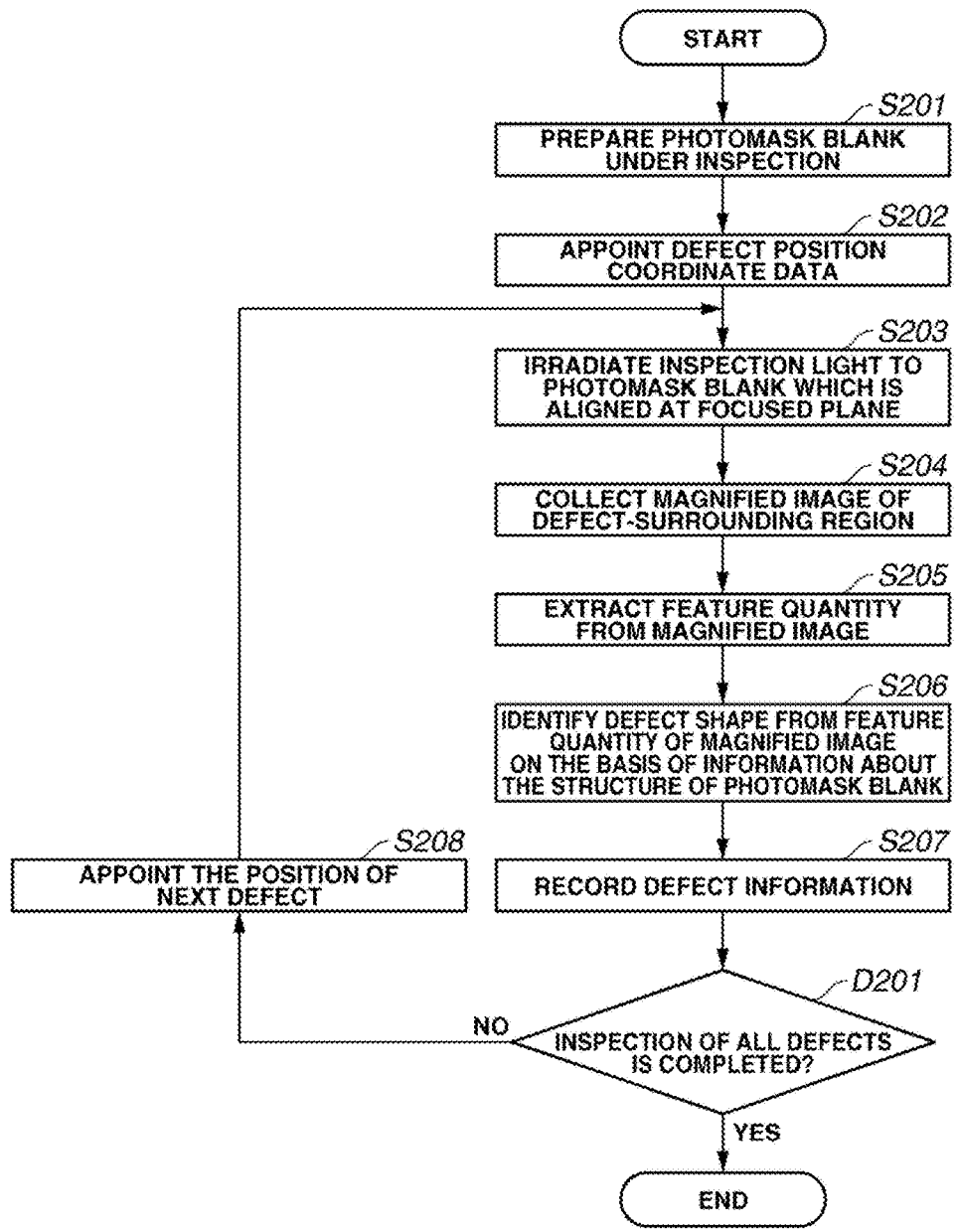

FIG.9

| FEATURE OF INSPECTION IMAGE | ↑⌒↓ | ↑⌒⌒→ | ↑⌒⌒→ | ↑⌒⌒→ |
|---|---|---|---|---|
| FILM STRUCTURE A | PINHOLE DEFECT | | | |
| FILM STRUCTURE B | BUMP DEFECT | PINHOLE DEFECT | | |
| FILM STRUCTURE C | | | BUMP DEFECT | PINHOLE DEFECT |
| FILM STRUCTURE D | | | BUMP DEFECT | PINHOLE DEFECT |

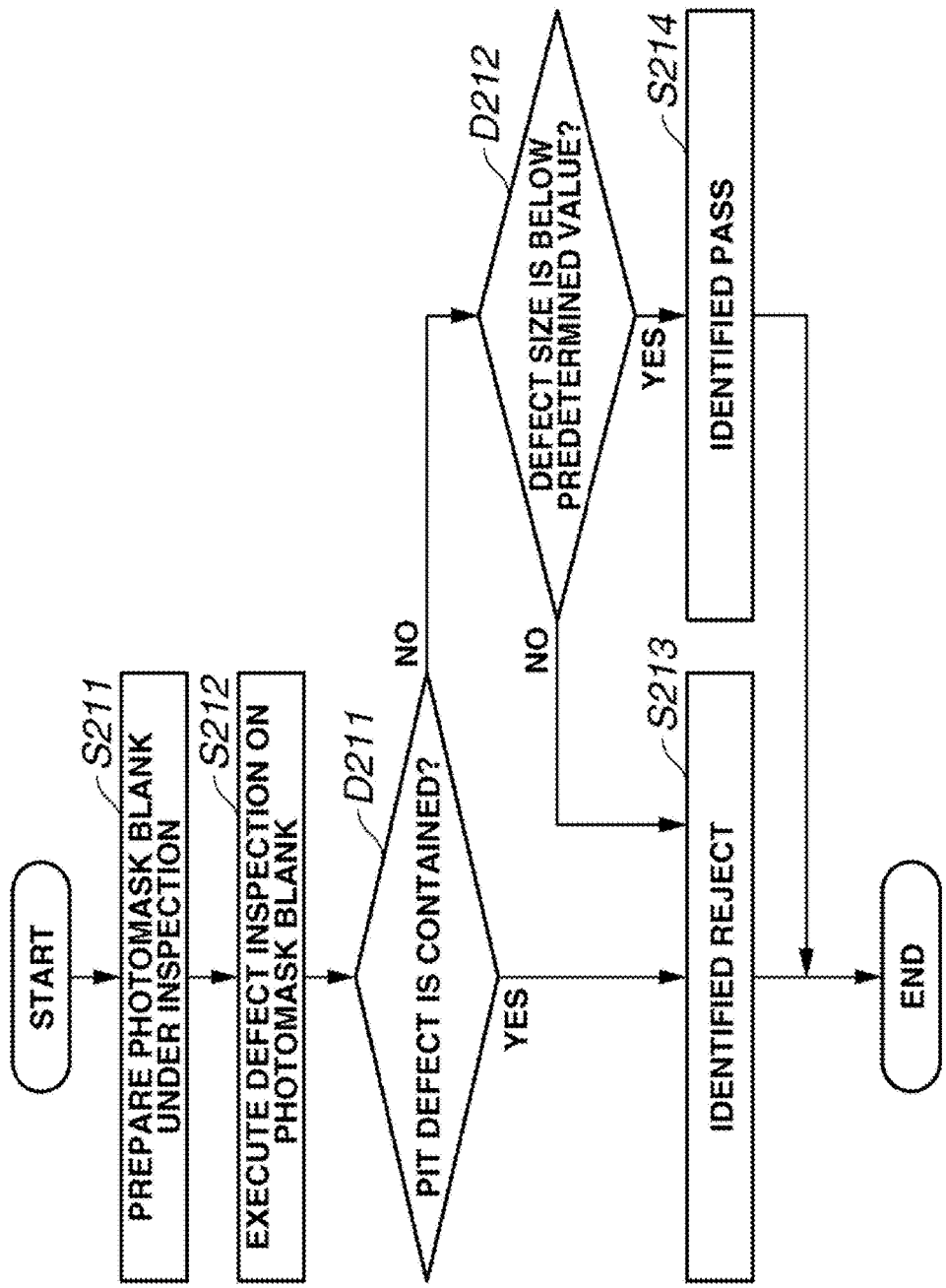

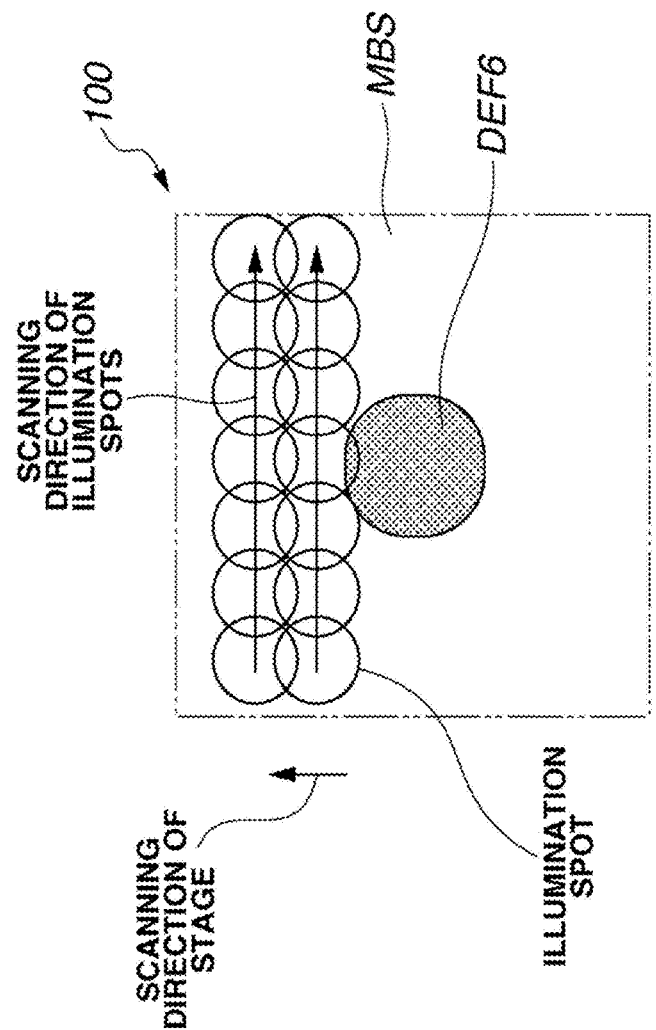

METHODS FOR DEFECT INSPECTION, SORTING, AND MANUFACTURING PHOTOMASK BLANK

CROSS-REFERENCE TO RELATED APPLICATION

This non-provisional application claims priority under 35 U.S.C. § 119(a) on Patent Application Nos. 2017-011779 and 2017-243900 filed in Japan on Jan. 26, 2017 and Dec. 20, 2017, respectively, the entire contents of which are hereby incorporated by reference.

TECHNICAL FIELD

This invention relates to a method for inspecting defects on photomask blanks from which are manufactured photomasks (transfer masks) for use in the fabrication of microelectronic devices (semiconductor devices) and more particularly, to a method for inspecting defects on a photomask blank having a thin film of up to 10 nm thick, which is effective for identifying the shape of a pit defect such as pinhole in the thin film. It also relates to methods for sorting and manufacturing photomask blanks using the defect inspection method.

BACKGROUND ART

Microelectronic devices (semiconductor devices) are fabricated by repeating the photolithography technology of irradiating exposure light to a pattern-transfer mask, typically a photomask having a circuit pattern drawn thereon, for transferring the circuit pattern to a semiconductor substrate or wafer through a reduction projection optical system. As the circuit pattern of semiconductor devices is successively miniaturized, the mainstream exposure light now becomes the argon fluoride (ArF) excimer laser of wavelength 193 nm. Now that the multi-patterning process of combining exposure steps and processing steps plural times is adopted, a pattern having a feature size which is fully smaller than the exposure wavelength can be eventually formed.

The pattern-transfer mask is manufactured by forming a circuit pattern on an optical film-bearing substrate (mask blank). The optical film (thin film) is generally a film based on a transition metal compound or a film based on a transition metal-containing silicon compound. Depending on a particular purpose, a film functioning as light-shielding film or a film functioning as phase shift film is selected. Also included is a hard mask film which is a processing aid film intended for the high-precision processing of an optical film.

Since pattern-transfer masks, typically photomasks is used as the original for the fabrication of semiconductor devices having a fine size pattern, the masks must be defect-free. This naturally requires that photomask blanks be defect-free. Circuit patterns are formed by depositing a resist film on a film-bearing photomask blank, processing the resist film and underlying film by the conventional lithography or EB lithography to finally form the pattern. In this sense, the resist film is also required to have no defects such as pinholes. Under the circumstances, efforts have been devoted to the technology for detecting defects on photomasks or photomask blanks.

Patent Documents 1 and 2 describe methods for detecting defects or foreign particles by irradiating laser light to a substrate and capturing the scattered reflection light. Also described is the technology of providing detection signals with asymmetry and identifying whether defects are bump or pit. Patent Document 3 discloses the inspection of a pattern on an optical mask using deep ultraviolet (DUV) light. Further Patent Document 4 describes the technique of dividing an inspection beam into a plurality of spots, scanning the spots on the substrate, and receiving the reflected beam by a photo-detector. Patent Document 5 discloses the technology of using extreme ultraviolet (EUV) light near wavelength of 13.5 nm for identifying the bump/pit shape of defects on an EUV mask blank.

CITATION LIST

Patent Document 1: JP-A 2001-174415
Patent Document 2: JP-A 2002-333313
Patent Document 3: JP-A 2005-265736 (U.S. Pat. No. 7,379,176)
Patent Document 4: JP-A 2013-019766
Patent Document 5: JP-A 2007-219130 (U.S. Pat. No. 7,630,068)

DISCLOSURE OF INVENTION

All the inspection systems described in Patent Documents 1 to 4 adopt optical defect detection, enabling broad range defect inspection in a relatively short time and identification of defects of bump/pit shape. With respect to the EUV mask blank, Patent Document 5 describes the method for identifying whether phase defects are of bump or pit shape.

As long as the inventors studied by an inspection experiment using an atomic force microscope and an electron microscope in combination, the prior art method of examining the arrangement of bright and dark parts in inspection signals from a photomask blank sometimes fails in identification of bump/pit shape. That is, in some inspection signals of pinhole defects, the positional arrangement relationship of bright and dark parts necessary for bump/pit shape discrimination is vague. Particularly in the defect inspection of a processing aid film which is formed for processing of advanced masks, that is, a hard mask film of up to 10 nm thick, the problem of difficult bump/pit shape identification is likely to occur.

Under the circumstances, practical inspection experiments using the inspection systems described in Patent Documents 1 to 4 do not always succeed in identifying the bump/pit shape of a defect at a high accuracy. The method of Patent Document 5 is applicable to phase defects inherent to EUV mask blanks, but with difficulty, to the photomask blanks used in the current mainstream ArF lithography. It is thus desired to establish the method for identifying the bump/pit shape of a defect in a hard mask thin film at a high accuracy, which is difficult with the prior art methods.

An object of the invention is to provide a method for optically inspecting a defect on a photomask blank for identifying whether the surface shape of the defect is bump or pit at a highly reliable manner, especially identifying whether the shape of a defect in a hard mask thin film (used as a processing aid film in mask pattern processing) is bump or pit, as well as methods for sorting and manufacturing photomask blanks by utilizing the method for identifying the bump/pit shape of a defect on a photomask blank and excluding pinhole defect-bearing substrates.

Making a study on the light intensity distribution of inspection signals from defects in various optical films from both the aspects of an inspection experiment and simulation, the inventors have found that a bright/dark change and a positional arrangement relationship of bright/dark parts in a defect observation image are different, depending on the values of complex refractive index with respect to inspection light of an optical film and an underlying optical film. The invention is predicated on this and further findings.

In one aspect, the invention provides a method for inspecting a defect on a photomask blank, comprising the steps of:

(A1) preparing a photomask blank having at least one thin film on an optically transparent substrate, the photomask blank bearing a defect on its surface, (A2) moving the photomask blank to move the defect on the photomask blank surface to a position observable by an inspection optical system, irradiating inspection light to a defect-bearing surface region, and collecting the reflected light from the irradiated region as a magnified image of the region via the inspection optical system, (A3) extracting a feature parameter from the magnified image, and (A4) identifying the shape of the defect on the basis of the feature parameter combined with the structure of the photomask blank thin film.

In a preferred embodiment, the magnified image in step (A2) is created by diffraction components of the reflected light that are transmitted through the inspection optical system, and higher-order diffraction components as said diffraction components are asymmetric between positive and negative sides with respect to the zeroth-order diffraction component (specular component) of the reflected light.

In a preferred embodiment, step (A3) includes a processing step of comparing a variation of the light intensity level of a defect area in the magnified image with the light intensity level of a defect-surrounding area, for thereby extracting the feature parameter from the defect inspection image which contains the intensity difference between a bright part with a high light intensity and a dark part with a low light intensity and the positional arrangement relationship between the bright part and the dark part.

Further preferably, in step (A4), the shape of the defect is identified on the basis of data including the feature parameter of the magnified image and the structure of the photomask blank thin film, and with reference to a table which is previously formed based on optical simulation or empirical data for enabling a choice between pinhole defect and bump defect.

In a preferred embodiment, provided that the outermost surface of the photomask blank under inspection is a thin film which is transparent to the inspection light, when a feature parameter indicating that the magnified image of the defect is a bright part-predominant image is extracted in step (A3), the defect detected is identified to be a pinhole defect.

In another preferred embodiment, provided that the photomask blank under inspection has a film structure that a thin film at the outermost surface has a higher reflectivity of inspection light than an underlying layer, when a feature parameter indicating that the magnified image of the defect is a dark part-predominant image is extracted in step (A3), the defect detected is identified to be a pinhole defect.

In a preferred embodiment, the thin film has a thickness of up to 10 nm; and the inspection light is light having a wavelength of 210 to 550 nm.

In another aspect, the invention provides a system for inspecting a defect on a photomask blank having at least one thin film on an optically transparent substrate, comprising an inspection system adapted to irradiate inspection light to a surface region of the thin film and to capture the reflected light from the irradiated region, for thereby inspecting any defects on the surface of the photomask blank, and a computer having installed therein a program for executing the steps in the photomask blank defect inspection method defined above.

In a further aspect, the invention provides a method of sorting photomask blanks, comprising sorting photomask blanks having no pinhole defects, based on the identification whether defects are of bump or pit shape by the inspection method defined above.

In a still further aspect, the invention provides a method for manufacturing a photomask blank, comprising the steps of forming at least one thin film on an optically transparent substrate to construct a photomask blank, and sorting a photomask blank having no pinhole defects by the sorting method defined above.

ADVANTAGEOUS EFFECTS OF INVENTION

The optical defect inspection method of the invention is effective for discriminating defects of bump or pit shape on a photomask blank in a highly reliable manner, for thereby identifying pit defect and pinhole defect which are fatal defects. The application of the defect inspection method ensures that photomask blanks having pit defects which are fatal defects are excluded, and photomask blanks having no fatal defects are available at lower costs and higher yields.

BRIEF DESCRIPTION OF DRAWINGS

FIGS. 4A and 4B illustrate a pit defect in the surface of a photomask blank and an exemplary observation image thereof, FIG. 4A being a cross-sectional view of a defect area of photomask blank, FIG. 4B being a cross-sectional view of the light intensity distribution of the inspection image.

FIGS. 6A to 6F illustrate the structure of the first film embodiment and cross-sectional profile of inspection image, FIG. 6A being a cross-sectional view of a photomask blank including an uppermost film and a film next thereto where a pit defect is present, FIG. 6B being a cross-sectional view of a photomask blank including an uppermost film on which a foreign particle is deposited, FIG. 6C being a cross-sectional view of a photomask blank including an uppermost film on which a bump defect of the same material as the uppermost film is present, FIGS. 6D, 6E and 6F being cross-sectional profiles of inspection images of the defects shown in FIGS. 6A, 6B and 6C, respectively.

FIG. 8 is a flow chart showing steps of one exemplary method for inspecting a defect on a photomask blank.

FIG. 9 is a table of a feature parameter of a defect inspection image, film embodiment, and defect shape.

FIG. 10 is a flow chart showing steps of one exemplary process for identifying whether a photomask blank is pass or reject.

FIG. 11 illustrates the scanning of illuminated spots for inspection.

DESCRIPTION OF PREFERRED EMBODIMENTS

Figure 1A:
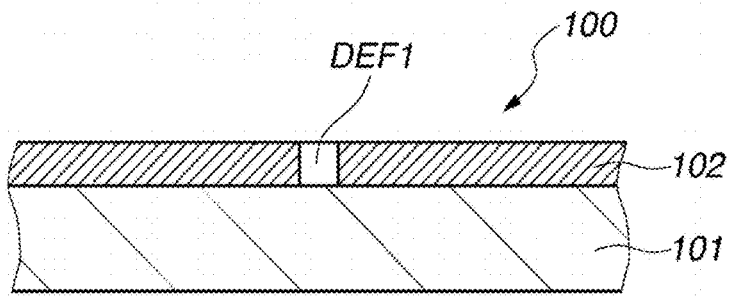
FIGS. 1A, 1B and 1C are cross-sectional views of defect-bearing photomask blanks, FIGS. 1A and 1B showing photomask blanks where a pinhole defect or pit defect is present, FIG. 1C showing a photomask blank where a bump defect is present.
Figure 1B:
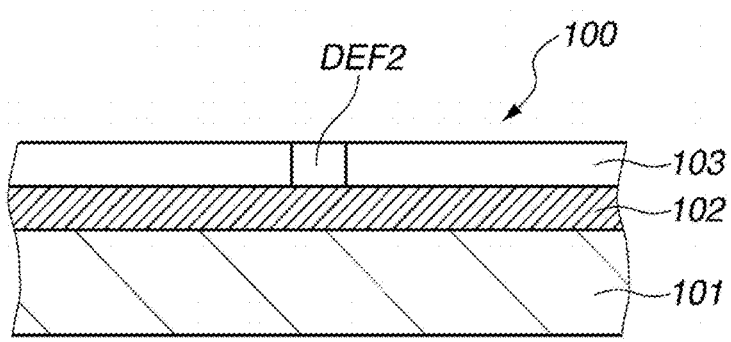

If a defect such as pinhole is present in a thin film of a photomask blank, that defect becomes the cause of a defect in a mask pattern on a photomask which is manufactured from the blank. One typical defect on a photomask blank is illustrated in FIG. 1. FIG. 1A shows a photomask blank 100 comprising a transparent substrate 101 and an optical thin film 102 formed thereon, which functions as a light-shielding film or a phase shift film (in the case of a halftone phase shift mask). A pinhole defect DEF1 is present in the thin film 102. FIG. 1B shows a photomask blank 100 comprising a transparent substrate 101, an optical thin film 102 formed thereon, which functions as a light-shielding film or a phase shift film (in the case of a halftone phase shift mask), and a processing aid film 103 which assists in high accuracy processing of the thin film 102. A pinhole defect DEF2 is present in the processing aid film 103. When a photomask is manufactured from such a photomask blank by the conventional method, the photomask bears a defect originating from the photomask blank. The defect on the photomask becomes the cause for inducing a pattern transfer error during lithographic exposure through the photomask. It is then necessary to detect the defect on the photomask blank prior to its processing, and thus to exclude the defect-bearing photomask blank or correct the defect.

Figure 1C:
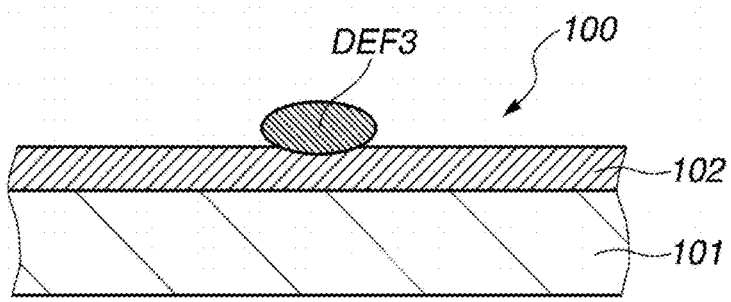

FIG. 1C shows an exemplary bump defect on a photomask blank. Illustrated is a photomask blank 100 having an optical thin film 102 on which a bump defect DEF3 is present. The defect DEF3 may be a bump defect integrated with the thin film 102 or a foreign bump defect (like foreign particle) deposited on the thin film 102. When a photomask is manufactured from such a photomask blank by the conventional method, a fatal pinhole defect is not always formed on the photomask. The foreign defect deposited on the film surface does not become a fatal defect if it is removable by cleaning.

As mentioned above, it becomes the key for guaranteeing the quality of photomask blanks and governing the manufacture yield thereof to identify whether a defect on a photomask blank is a pit defect (like pinhole) which is a fatal defect or a bump defect which is not necessarily a fatal defect. There is thus the desire for a method capable of discriminating the bump/pit shape of a defect via a short time optical inspection process at a high reliability. Now that the wavelength of exposure light used in the current mainstream lithography is 193 nm of ArF excimer laser, a method capable of discriminating the bump/pit shape of a defect having a size of up to 200 nm, preferably up to 100 nm on a mask blank is desired.

Figure 2:
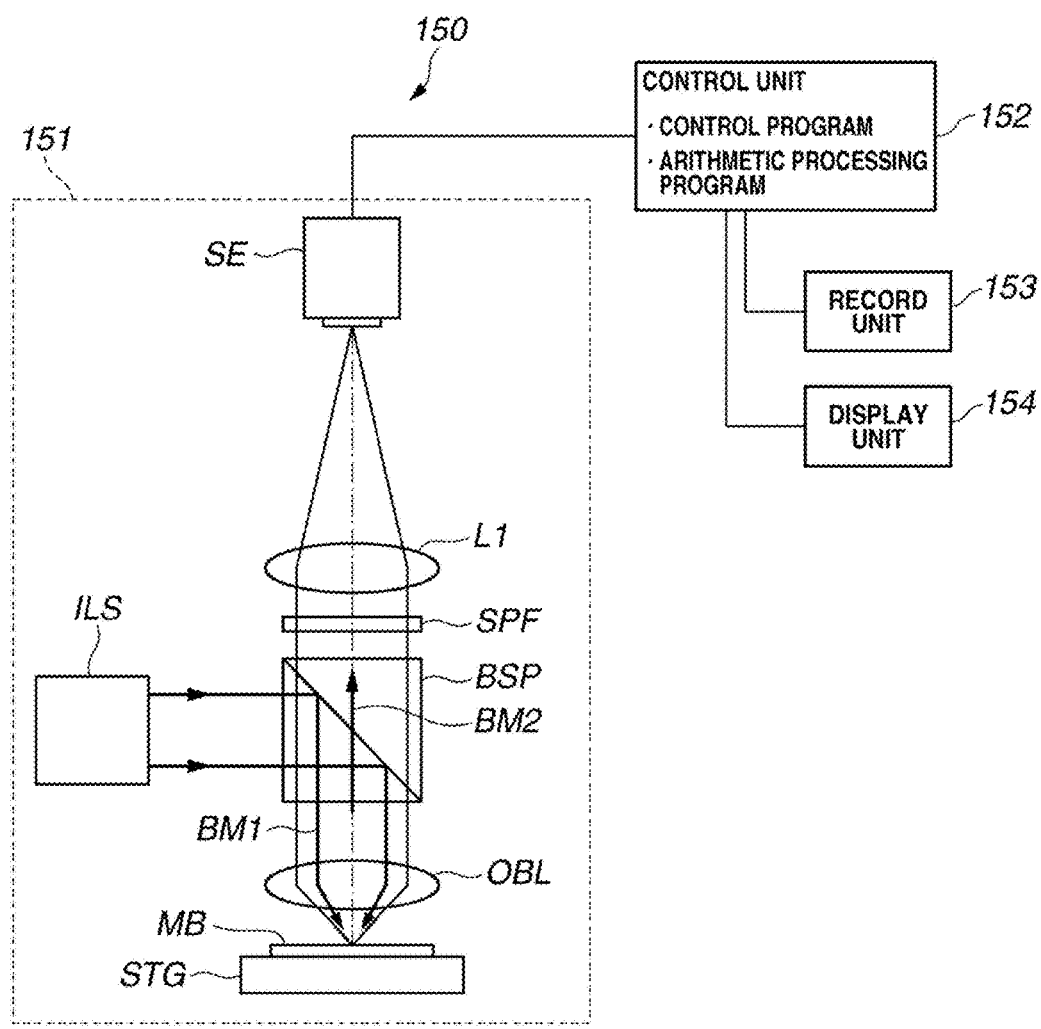
FIG. 2 schematically illustrates one exemplary inspection system for use in the photomask blank defect inspection method.

First described is an inspection system advantageously used in the defect inspection of photomask blanks, specifically an inspection system used for identifying the bump/pit shape of a defect in a surface portion of a photomask blank. FIG. 2 is a block diagram showing an exemplary basic construction of a defect inspection system 150, mainly comprising an inspection optical unit 151, a control unit 152, a recording unit 153, and a display unit 154. The inspection optical unit 151 includes a light source ILS capable of emitting inspection light, a beam splitter BSP, an objective lens OBL, a stage STG on which a photomask blank MB is rested for motion, and an image sensor SE. The light source ILS is designed to emit inspection light BM1 having a wavelength of about 210 to 550 nm. The inspection light BM1 from light source ILS is bent by beam splitter BSP and directed to irradiate a selected region on photomask blank MB through objective lens OBL. Light BM2 reflected by the surface of photomask blank MB is collected by objective lens OBL, whereupon it passes through beam splitter BSP and a lens L1 and reaches the light receiving surface of image sensor SE. The position of image sensor SE is adjusted such that a magnified inspection image of the selected surface region of mask blank MB is formed on the light receiving surface of image sensor SE. The data of the magnified inspection image collected by image sensor SE are subjected to image processing operation whereby the size of the defect is computed and the bump/pit shape of the defect is identified, with the results being recorded as defect information. The inspection system 150 operates under the control of control unit 152. The control unit 152 has installed therein a control program and various image processing arithmetic programs and controls the operation of recording unit 153 for storing inspection data and display unit 154 for providing various displays.

A magnified inspection image may be collected by the direct method of using image sensor SE in the form of a sensor (e.g., CCD camera) comprising a multiplicity of photodetectors arranged as pixels and collecting magnified images which are formed by light BM2 reflected from the surface of photomask blank MB via objective lens OBL, all together as a two-dimensional image. Also adoptable is a method of converging the inspection light BM1 at the surface of photomask blank MB to create illuminated spots, giving a scanning function to the inspection light-emitting source ILS, scanning the surface with a series of illuminated spots, sequentially collecting the light intensity of reflected light BM2 by image sensor SE, photo-electric conversion and recording, thereby creating an overall two-dimensional image.

When the reflected light BM2 is collected for identifying the bump/pit shape of a defect, higher-order diffraction components being asymmetric between positive and negative sides with respect to the zeroth-order diffraction component (specular component), in other words, at the center of specular light, of the reflected light may be collected as the diffraction components. More particularly, there may be adopted the method of directing the chief ray of inspection light BM1 to illuminate the surface of photomask blank MB as oblique incidence or the method of inserting a spatial filter SPF for shielding a portion of the beam of reflected light BM2 while maintaining the chief ray as vertical illumination, and letting image sensor SE capture the magnified inspection image. By adopting one of these methods, it is generally possible to identify the bump/pit shape of a defect from the positional relationship or light intensity difference between bright and dark parts in the inspection image light intensity distribution.

Next, with respect to the inspection image obtained by converging inspection light BM1, with its chief ray maintained as vertical illumination, at the surface of photomask blank MB while scanning, and sequentially collecting the light intensity of reflected light BM2, the difference between bump and pit defects inspection images is described. It is now assumed that the right half of flux of reflected light BM2 advancing toward image sensor SE is shielded by the function of spatial filter SPF when the light intensity of reflected light BM2 is collected.

Figure 3A:
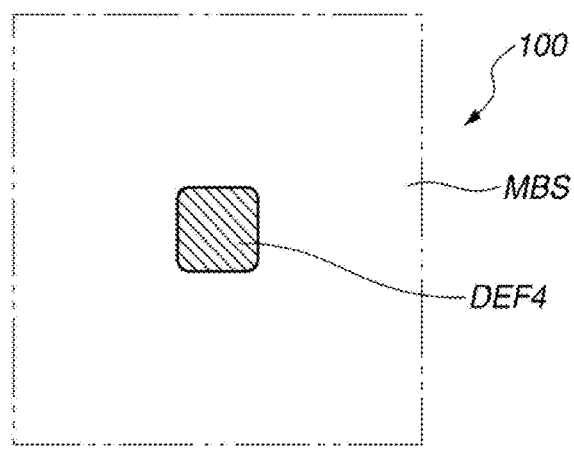
FIGS. 3A to 3D illustrate a bump defect on the surface of a photomask blank and an exemplary inspection image thereof, FIGS. 3A and 3B being plan and cross-sectional views of a defect area of photomask blank, FIG. 3C being an inspection image of the bump defect, FIG. 3D being a cross-sectional view of the light intensity distribution of the inspection image.
Figure 3B:
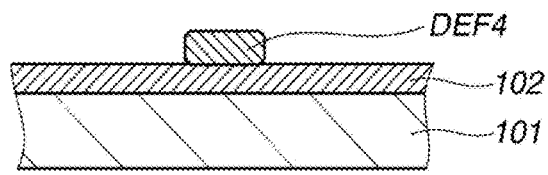

FIGS. 3A and 3B are plan and cross-sectional views of a photomask blank 100 having a bump defect DEF4, respectively. The photomask blank 100 includes a transparent substrate 101 which is transparent to inspection light, such as a quartz substrate, and an optical thin film 102 of MoSi base material formed thereon. A bump defect DEF4 of MoSi base material or another material is present on a surface MBS of the thin film 102.

Figure 3C:
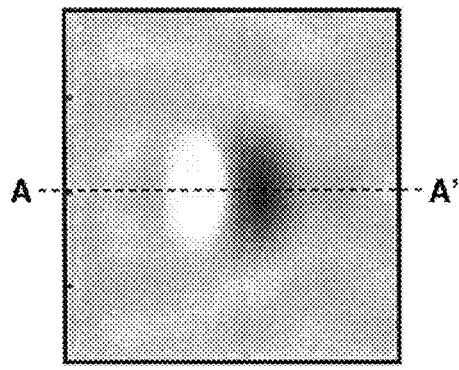
Figure 3D:
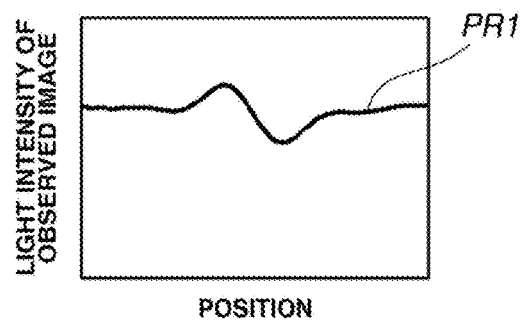

When the photomask blank surface MBS bearing the bump defect DEF4 is illuminated and scanned with converged inspection light BM1, and the reflected light is collected through spatial filter SPF, there is obtained an inspection image having a light intensity distribution as shown in FIG. 3C. The light intensity distribution in a cross section along line A-A' in FIG. 3C has a cross-sectional profile PR1 as shown in FIG. 3D. The cross-sectional profile PR1 has a bump defect-inherent configuration including a bright part at the left side and a dark part at the right side of bump defect DEF4.

Similarly, FIG. 4A is a cross-sectional view of a photomask blank 100 having a pit defect DEF5, and FIG. 4B is a diagram showing a cross-sectional profile PR2 of the light intensity distribution of the inspection image obtained therefrom. The cross-sectional profile PR2 has a pit defect-inherent configuration including a dark part at the left side and a bright part at the right side of pit defect DEF5.

However, depending on the film embodiment of the photomask blank, there is a case where it is impossible to correctly identify, in terms of only the positional relationship of bright/dark parts in the inspection image, whether the defect is bump or pit. An example of this case is described below.

First Film Embodiment

Figure 5A:
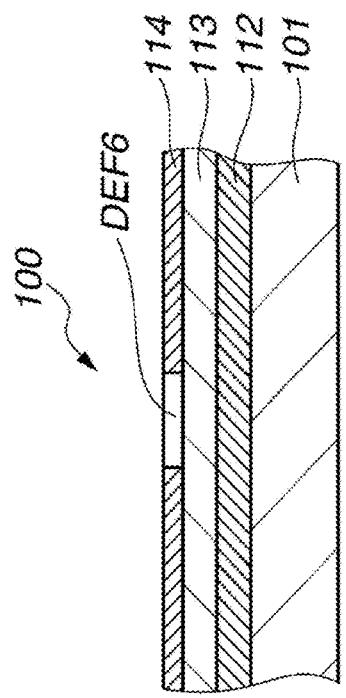
FIGS. 5A and 5B illustrate the structure of a first film embodiment and cross-sectional profile of inspection image, FIG. 5A being a cross-sectional view of a photomask blank including an uppermost film where a pinhole defect or pit defect is present, FIG. 5B being a cross-sectional profile of an inspection image of the pit defect.
Figure 5B:
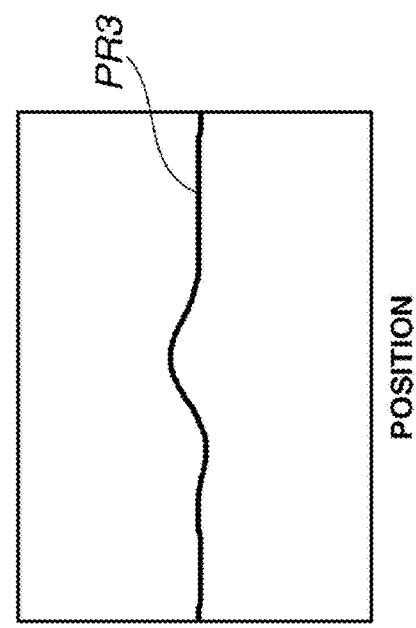

FIG. 5A is a cross-sectional view of a photomask blank 100 bearing a pit defect. The photomask blank 100 includes a transparent substrate 101 which is transparent to inspection light, such as quartz substrate, an optical thin film 112 of MoSi base material, an optical thin film 113 of Cr base material, and a hard mask thin film 114 of a material which is substantially transparent to inspection light, such as silicon oxide, having a thickness of about 5 to 10 nm, formed on the substrate in order, wherein a pit defect DEF6 such as pinhole defect is present in the hard mask thin film 114. When the photomask blank surface bearing the pit defect DEF6 is illuminated and scanned with the converged inspection light, and the reflected light is collected through spatial filter SPF, there is obtained an inspection image. The light intensity distribution of the inspection image has a cross-sectional profile PR3 as shown in FIG. 5B. The light intensity distribution of the inspection image includes substantially only a bright part at the site of pit defect DEF6. The positional relationship of bright/dark parts in the light intensity distribution of the inspection image of a typical pit defect as shown in FIG. 4 does not appear.

It is noted that even when a film structure is the same as the structure shown in FIG. 5A, a variety of inspection images are obtained as exemplified in FIG. 6, depending on the type of defects. FIG. 6A shows that a pit defect is already present in an optical thin film 113 of Cr base material, a defectless hard mask thin film 114 of uniform thickness is formed on the optical thin film 113, and as a result, a defect DEF7 of pit shape is present on the surface of thin film 114. FIG. 6B shows that although the hard mask thin film 114 is defectless until the end of its formation, a foreign particle based on silicon deposits on the surface of hard mask thin film 114 as a bump defect DEF8. Further FIG. 6C shows that the surface of a hard mask thin film 114 is partially raised as a bump defect DEF9. The cross-sectional profiles of inspection images of these defects DEF7, DEF8 and DEF9 are a profile PR4 shown in FIG. 6D, a profile PR5 shown in FIG. 6E, and a profile PR6 shown in FIG. 6F. Profile PR4 is the inspection image where a typical pit defect is present, but the hard mask thin film 114 at the outermost surface is defectless; profile PR5 is the inspection image of a typical bump defect; and profile PR6 is apparently the inspection image of a pit defect, but it is a bump defect in hard mask thin film 114 which is transparent to inspection light, when this profile PR6 is obtained from the first film embodiment.

As is evident from the foregoing, when an inspection image where a bright part is predominant is obtained as the defect inspection image in the first film embodiment, it can be identified that a pinhole defect which is a fatal defect is present. The criterion of identification between bump/pit defect in the first film embodiment is different from the criterion used in the case of typical bump and pit defects as shown in FIGS. 3 and 4. It is an identification criterion inherent to the first film embodiment. The criterion is further effective where a film of a material which is substantially transparent to inspection light has a reduced thickness, for example, a thickness of up to 10 nm, especially 5 to 10 nm.

Second Film Embodiment

Figure 7A:
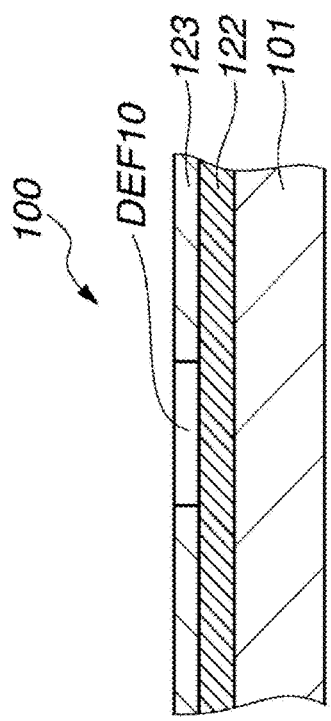
FIGS. 7A and 7B illustrate the structure of a second film embodiment and cross-sectional profile of inspection image, FIG. 7A being a cross-sectional view of a photomask blank including an uppermost film where a pinhole defect is present, FIG. 7B being a cross-sectional profile of an inspection image of the defect.
Figure 7B:
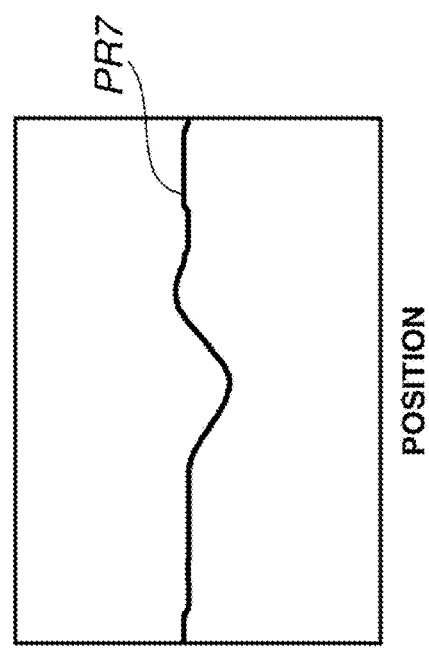

FIG. 7A is a cross-sectional view of a photomask blank 100 bearing a pit defect. The photomask blank 100 includes a transparent substrate 101 which is transparent to inspection light, such as quartz substrate, an optical thin film 122 of MoSi base material, and a hard mask thin film 123 of Cr base material having a thickness of about 10 nm, formed on the substrate in order, wherein a pit defect DEF10 such as pinhole defect is present in the hard mask thin film 123. The second film embodiment is characterized in that the hard mask thin film 123 has a higher reflectivity of inspection light than the optical thin film 122. When the photomask blank surface bearing the pit defect DEF10 is illuminated and scanned with converged inspection light, and the reflected light is collected through spatial filter SPF, there is obtained an inspection image, with its light intensity distribution having a cross-sectional profile PR7 as shown in FIG. 7B. The light intensity distribution of the inspection image includes substantially only a dark part at the site of pit defect DEF10. There does not appear the positional relationship of bright/dark parts in the light intensity distribution of the inspection image of a typical pit defect as shown in FIG. 4. The reason why the pit defect is observed only as a dark part is that pit defect DEF10 is shallow, so that the quantity of reflected light from the side of the defect is small, and the influence of reflectivity of inspection light on a light intensity variation becomes more significant.

Notably, where a bump defect is present on the hard mask thin film 123, its inspection image is an inspection image with the positional relationship of bright and dark parts equivalent to the profile PR1 shown in FIG. 3D.

As is evident from the foregoing, when an inspection image where the dark part is predominant is obtained as the defect inspection image in the second film embodiment, it can be identified that a pinhole defect which is a fatal defect is present. The criterion of identification between bump defect and pit defect in the second film embodiment is different from that used in the case of typical bump defect and pit defect as shown in FIGS. 3 and 4. It is a specific identification criterion in the second film embodiment.

Next, the defect inspection method of the invention is described in more detail in accordance with the flow chart of FIG. 8. First step (A1) is to prepare a photomask blank having a defect to be inspected (referred to as photomask blank under inspection, hereinafter) (step S201). Then data indicative of positional coordinates of the defect on the photomask blank is taken in (step S202). As the positional coordinates of the defect, positional coordinates of the defect separately determined by a well-known defect inspection method may be utilized.

Next step (A2) is to align the position of the defect with the inspection site of the inspection optical unit, and irradiate inspection light from above the photomask blank via the objective lens (step S203) and to collect the reflected light from the inspection light-illuminated region through the objective lens as a magnified image of the defect-surrounding region (step S204). Alignment may also be achieved by resting the photomask blank under inspection on a stage which is movable in a in-plane direction, moving the stage in the in-plane direction on the basis of the positional coordinates of the defect on the photomask blank under inspection, and maintaining the defect on the focused plane of the objective lens of the inspection optical unit.

Next, from the light intensity distribution (image data or cross-sectional profile) of the magnified image thus collected, the feature of a light intensity changing portion in the inspection image at the defect area, that is, the feature quantity of the magnified image is extracted (step S205).

Thereafter, step (A4) is to identify the bump/pit shape of the defect on the basis of the feature quantity of the magnified image extracted in step S205 and the film structure (or film embodiment) of the photomask blank (step S206). Examples of the bump/pit shape identification step will be described later. Notably, the defect size may be forecast from well-known image processing of the inspection image. The bump/pit shape of defect and the forecast value of defect size are recorded as defect information along with the defect positional coordinates (step S207).

Next, it is identified whether or not inspection is completed on all defects on the basis of the data of defect positional coordinates previously taken in (identification D201). If not completed, a new defect position is assigned (step S208), the process goes back to step S203 where collection of inspection image data and identification between bump/pit shape of the defect are repeated. If it is identified that inspection is completed on all the defects previously taken in (identification D201), the defect inspection ends.

Next, the step of identification between bump/pit shape is described. The recording unit 153 connected to control unit 152 of the defect inspection system shown in FIG. 2 stores the defect data and a table representing the relationship of the features of inspection signals upon defect detection to the various optical film (thin film) structures of photomask blanks as shown in FIG. 9. The features of inspection signals include an image wherein a bright part is predominant at the defect area, an image wherein a dark part is predominant at the defect area, an image consisting of a bright part at the left and a dark part at the right, and an image consisting of a dark part at the left and a bright part at the right. The structures of optical film (thin film) include, for example, film structure A which is the film embodiment 1 described above, that is, a structure in which a hard mask thin film which is transparent to inspection light and has a thickness of up to 10 nm is formed at the outermost surface; film structure B which is the film embodiment 2 described above, that is, a structure in which a hard mask thin film formed at the outermost surface having a thickness of up to 10 nm has a higher reflectivity of inspection light than the underlying optical thin film; film structure C, that is, a structure in which an optical thin film of MoSi base material is formed at the outermost surface; and film structure D, that is, a structure in which an optical thin film of Cr base material having a thickness of at least 20 nm is formed at the outermost surface.

Referring to the table of FIG. 9, for any of various film structures, extracting the feature of the inspection image obtained from defect inspection makes it possible to discriminate whether the defect on the film is a fatal pinhole defect or a bump defect. That is, since the feature quantity of the magnified image is extracted in the previous step S205, the step S206 for identifying the bump/pit shape of a defect is capable of discriminating the bump/pit shape of a defect by referring to the table of FIG. 9 for identifying the type of defect from the film structure of the substrate under inspection and the feature of the magnified image. In particular, it can be identified whether or not the defect is a fatal pinhole defect.

It is noted that in some cases, the identification criterion of pit defect in the table of FIG. 9 varies depending on the extent of light shielding by spatial filter SPF. For example, in film structures C and D, when the light shielding portions of the spatial filter are set inverse on the left and right, the identification of pit defect or bump defect corresponding to the positional arrangement of bright and dark parts which is the feature of the magnified image is also inversed.

The table is not limited to the cross-sectional profile of an inspection image, and may be an image of two-dimensional light intensity distribution. Further, sequential addition in compliance with the past results of defect inspection and the introduction of a novel film embodiment is also possible.

Next, the method for sorting photomasks using the defect inspection method of the invention is described according to the flow chart of FIG. 10. First, a photomask blank under inspection is prepared (step S211). Subsequently, the above-mentioned defect inspection is carried out on the photomask blank, and the defect data including the bump/pit shape and size of all defects detected are recorded (step S212). Then it is examined if pit defects such as pinhole defects are contained in the recorded defect data (identification D211). If pit defects are contained, that photomask blank is sorted as a reject (step S213). If pit defects are not contained, and further if it is identified that the forecast size of defect is not greater than the predetermined permissible value (identification D212), that photomask blank is sorted as a pass (step S214). Inversely, if it is identified that the forecast size of defect is greater than the predetermined permissible value (identification D212), that photomask blank is sorted as a reject (step S213).

In the case of a photomask blank having a thin film with a thickness of up to 10 nm, typically a hard mask thin film formed at the outermost surface, the defect inspection method is capable of discriminating the bump/pit shape of a defect at a high reliability level by extracting a feature quantity of a defect inspection image (magnified image), and referring to the table for determining the bump/pit shape of defect inherent to the film embodiment.

When the inventive defect inspection method capable of discriminating the bump/pit shape of a defect at a high reliability level is applied to the photomask blank manufacturing process, photomask blanks having no pit defect such as pinhole defect can be sorted by removing those photomask blanks having a pit defect such as pinhole defect at a high reliability level. The data of the bump/pit shape of a defect obtained in the inventive defect inspection method may be imparted to the photomask blanks such as by attaching inspection tags.

In the prior art, since the understanding that the observation image of a pinhole defect differs depending on the film structure was insufficient, there was a possibility that fatal pinhole defects are overlooked, or photomask blanks having a defect which is not necessarily a fatal defect are excluded as reject. This was a cause of low yields. According to the inventive defect inspection method wherein those photomask blanks having a pit defect which is a fatal defect are selectively excluded, photomask blanks meeting the product specifications are available in high yields.

EXAMPLES

Examples of the invention are given below by way of illustration, but not by way of limitation.

Example 1

Defect inspection was performed on a photomask blank of the first film embodiment having pit defects and bump defects. The inspection system used was the system 150 including the inspection optical unit 151 shown in FIG. 2. The light source ILS emits inspection light BM1 of wavelength 532 nm. The objective lens OBL has a numerical aperture NA of 0.95. The inspection light BM1 is converged through objective lens OBL to illuminate photomask blank MB from above. As shown in FIG. 11, the surface MBS of photomask blank MB (or 100) containing defect DEF6 was unidirectionally scanned with the converged light as illumination spots by scanning means (not shown). On the other hand, stage STG on which photomask blank MB was rested was intermittently or continuously moved in a direction perpendicular to the scanning direction. By a combination of scanning of illumination spots with movement of the stage, the predetermined region containing defects was scanned with illumination spots in a two-dimensional way. The reflected light from the photomask blank at each illumination spot was passed and converged through objective lens OBL, spatial filter SPF for shielding the right half of the reflected light, and lens L1 whereupon the intensity of the reflected light was detected by image sensor SE. The light intensities thus collected were arranged at the positions of illumination spots in a two-dimensional way, creating an inspection image (magnified image) of a defect. The illumination spots on the mask blank surface had a size of about 400 nm, and the two-dimensional scan region containing defects was a rectangular region of about 30 µm×30 µm.

Figure 12A:
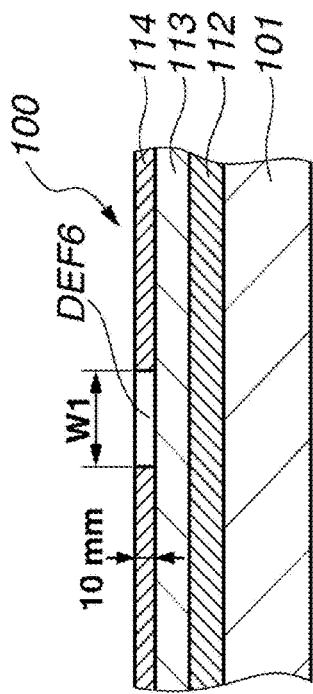
FIG. 12A is a cross-sectional view of a photomask blank having a pit defect in Example 1.
Figure 12B:
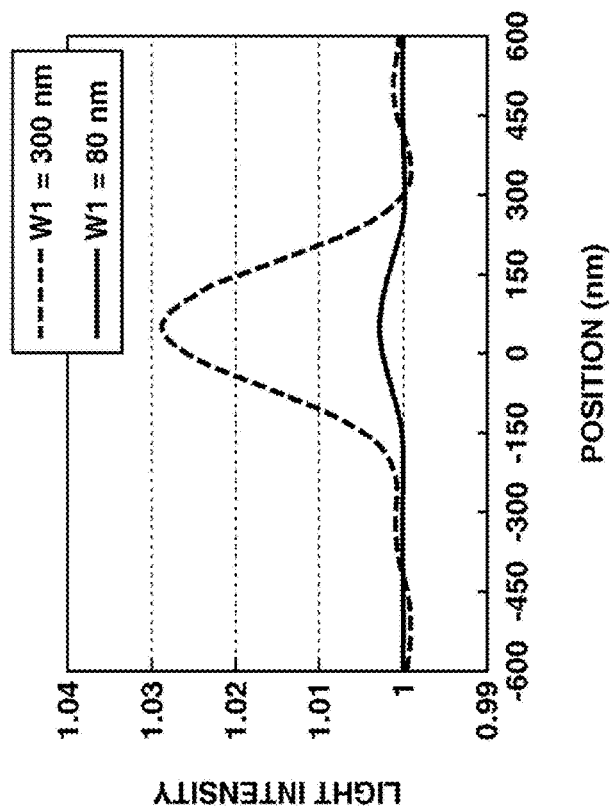
FIG. 12B is a cross-sectional profile showing the light intensity distribution of a defect inspection image.

FIG. 12A is a cross-sectional view of a photomask blank 100 of the first film embodiment having pinhole defects, the photomask blank 100 comprising a quartz substrate 101 which is transparent to inspection light, and an optical thin film 112 of MoSi base material having a thickness of 75 nm, an optical thin film 113 of Cr base material having a thickness of 44 nm, and a hard mask thin film 114 of silicon oxide having a thickness of 10 nm formed thereon wherein a pinhole defect DEF6 having a diameter W1 is present in the hard mask thin film 114. On the assumption that the defect has a size (or diameter) W1=80 nm and 300 nm, the region containing such defects is scanned with the illumination spots whereby a magnified inspection image is obtained as the sequence of reflected light intensities corresponding to the scanning positions. FIG. 12B is a cross-sectional profile of the magnified inspection image of the region containing the defect. This magnified image is characterized in that for each defect size W1, there appears a profile that a dark part is not substantially appeared and a bright part is predominant on the basis of the reflected light intensity of the defect-free region. Since the hard mask thin film 114 is substantially transparent to the inspection light, it functions as an anti-reflective film. Therefore, the hard mask thin film 114 has a reduced reflectivity at its surface, the reflectivity of the pinhole defect area through which the surface of the underlying layer is exposed is higher than that of the surrounding portion. As a result, the pinhole part in the inspection image became a bright part. Although the true bump/pit shape of the defect is unclear at the stage when the photomask blank is inspected, the defect is identified to be a pinhole defect based on that the photomask blank under inspection is an optical thin film structure of the first film embodiment and the feature of the defect observation image (magnified image) is the predominance of bright part, and with reference to the table of FIG. 9.

Figure 13A:
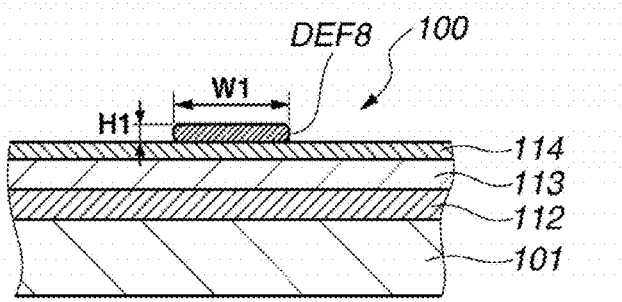
FIG. 13A is a cross-sectional view of a photomask blank having a bump defect in Example 1.
Figure 13B:
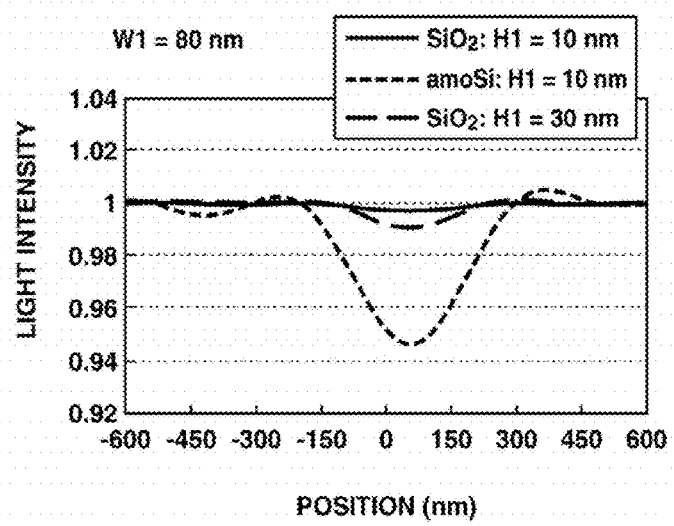
FIG. 13B is a cross-sectional profile showing the light intensity distribution of an inspection image of a defect.

FIG. 13A is a cross-sectional view of a photomask blank 100 having a film structure of the same first film embodiment as FIG. 12A, but having a bump defect DEF8. As the composition of the bump defect part, two compositions, the same composition as the hard mask thin film 114 of silicon oxide and amorphous silicon (Si) are appointed. On the assumption that the bump defect DEF8 has a width W1 of 80 nm and a height H1 of 10 nm and 30 nm, FIG. 13B is a cross-sectional profile of the magnified inspection image of the region containing the defect. In the magnified inspection image of the bump defect with W1=80 nm, although the intensity level varies depending on the height and composition, the defect area gives an inspection image where a dark part is predominant, whose profile is different from that of the inspection image of a pinhole defect shown in FIG. 12B. Therefore, the bump defect is distinguished from the pinhole defect.

Figure 13C:
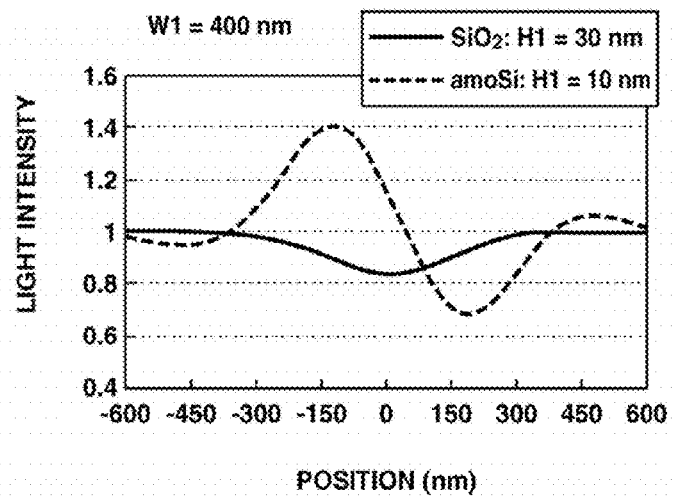
FIG. 13C is a cross-sectional profile showing the light intensity distribution of an inspection image of a different size defect.

On the assumption that the bump defect has a size W1=400 nm, FIG. 13C illustrates a cross-sectional profile of the magnified inspection image of the region containing the defect. It is also assumed that the defect has a height H1=30 nm when its composition is silicon oxide and a height H1=10 nm when its composition is amorphous silicon. An inspection image where the defect area becomes a dark part is obtained when the composition is silicon oxide, and the defect area gives an inspection image where a bright part and a dark part are juxtaposed is obtained when the composition is amorphous silicon. Both the images are different from the inspection image of a pinhole defect and thus distinguished therefrom.

By performing arithmetic operation utilizing the profile and the contrast of an inspection image, the defect size can be forecast from the inspection image. When the inspection image shown in FIG. 13C is obtained in the inspection step of the mask blank manufacture, the defect size is estimated to have a value in excess of 300 nm. Provided that the permissible defect size is 100 nm, for example, it is identified that there is present a bump defect which is not a fatal pinhole defect, but exceeds the permissible value. Then the photomask blank is sorted as a reject.

As understood from the above, in a photomask blank comprising a hard mask thin film having an antireflective film function formed on an optical thin film, the defect is a fatal pinhole defect when the inspection image of the defect has a light intensity distribution where a bright part is predominant, and the defect is a bump defect when the inspection image of the defect has a light intensity distribution where a dark part is predominant or there are a bright part on the left and a dark part on the right. These data were stored in the table of FIG. 9 as the feature of the magnified inspection image for film structure A. In defect inspection in the first film embodiment, a right identification between bump and pit shapes could be made by referring to film structure A in the table, that is, a fatal pinhole defect could be identified.

Example 2

Figure 14A:
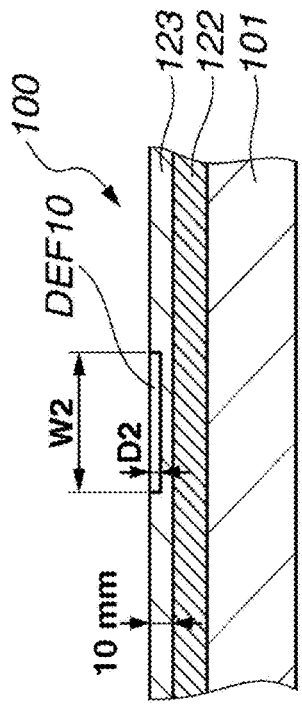
FIG. 14A is a cross-sectional view of a photomask blank having a pit defect in Example 2.

Defect inspection was performed on a photomask blank of the second film embodiment having pit defects and bump defects. The inspection system used was the system 150 including the inspection optical unit 151 shown in FIG. 2. The inspection optical unit wherein the inspection light BM1 is of wavelength 355 nm and the objective lens OBL has a numerical aperture NA of 0.85 provides a higher resolution than the unit used in Example 1, and the illuminated spot has a size of about 380 nm. The two-dimensional scan region was the same as in Example 1. FIG. 14A is a cross-sectional view of a photomask blank 100 comprising a quartz substrate 101 which is transparent to inspection light, and an optical thin film 122 of MoSi base material having a thickness of 75 nm, and a hard mask thin film 123 of Cr base material having a thickness of 10 nm formed thereon wherein a pit defect DEF10 such as pinhole defect is present in the hard mask thin film 123.

Figure 14B:
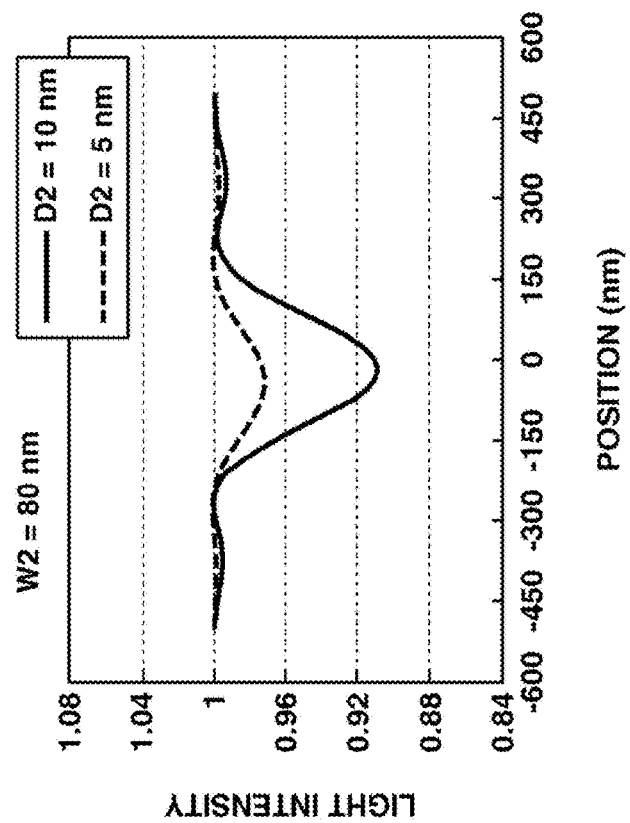
FIG. 14B is a cross-sectional profile showing the light intensity distribution of a defect inspection image.

On the assumption that the pit defect DEF10 has a width of 80 nm and a depth D2 of 5 nm (pit defect penetrating partly through the hard mask thin film 123) and 10 nm (pit defect penetrating throughout the hard mask thin film 123), FIG. 14B is a cross-sectional profile of light intensity of the inspection image of the region containing the defect. In either of the depths, the defect inspection image had a profile where a dark part was predominant and no bright part appeared.

Figure 15A:
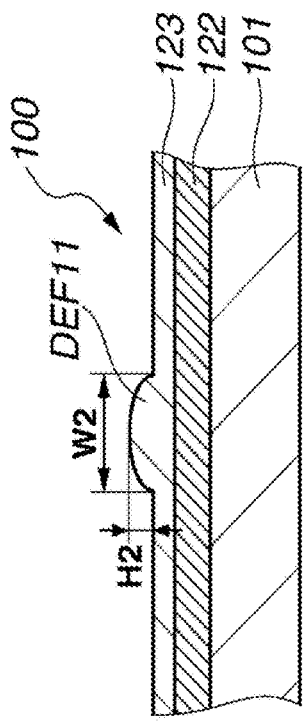
FIG. 15A is a cross-sectional view of a photomask blank having a bump defect in Example 2.
Figure 15B:
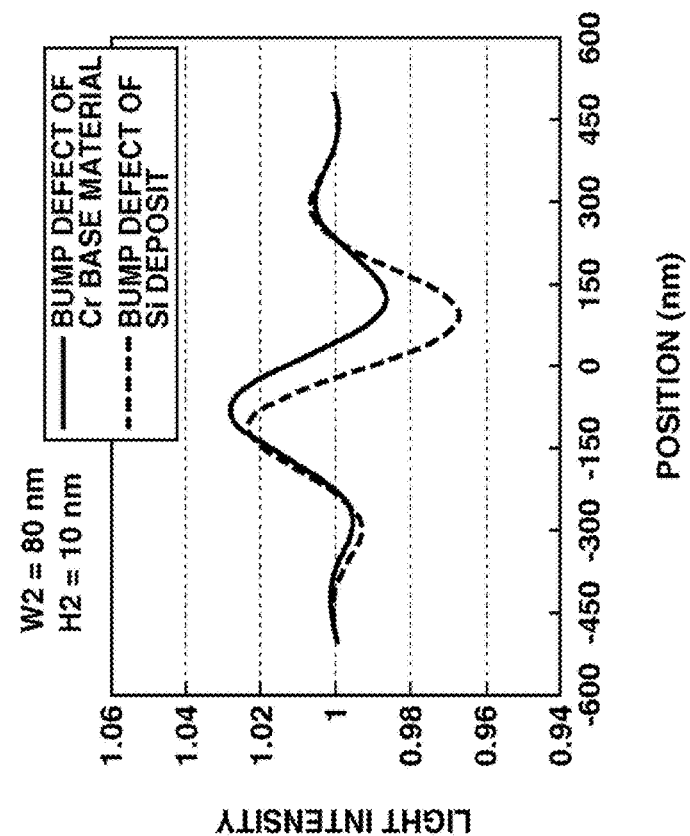
FIG. 15B is a cross-sectional profile showing the light intensity distribution of a defect inspection image.

FIG. 15A is a cross-sectional view of a photomask blank 100 having a film structure of the same second film embodiment as in FIG. 14A, but having a bump defect DEF11. As the composition of the bump defect DEF11, two compositions, the same composition as the hard mask thin film 123 of Cr base material and foreign particles (silicon particles) are appointed. On the assumption that the bump defect DEF11 has a width W2 of 80 nm and a height H2 of 10 nm, FIG. 15B is a cross-sectional profile of the magnified inspection image of the region containing the defect. In the magnified inspection image of the bump defect, for both the compositions, the defect area gives an inspection image where there are a bright part on the left and a dark part on the right. Although the intensity level varies depending on the composition, there is obtained a positional relationship between bright and dark parts similar to the typical light intensity distribution (cross-sectional profile PR1) of a bump defect shown in FIG. 3D.

As understood from the above, in a photomask blank comprising a thin film composed of high reflectivity material such as a hard mask thin film formed on an optical thin film, the defect is a fatal pinhole defect when the inspection image of the defect has a light intensity distribution where a dark part is predominant, and the defect is a bump defect when the inspection image of the defect has a light intensity distribution where there are a bright part on the left and a dark part on the right.

These data at the inspection wavelength 355 nm were stored in the table of FIG. 9 as the feature of the magnified inspection image for film structure B. In defect inspection in the second film embodiment, a right identification between bump and pit shapes could be made by referring to film structure B in the table, that is, a fatal pinhole defect could be identified.

Japanese Patent Application Nos. 2017-011779 and 2017-243900 are incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A method for inspecting a defect on a photomask blank, comprising the steps of:
   (A1) preparing a photomask blank having at least one thin film on an optically transparent substrate, the photomask blank bearing a defect on its surface,
   (A2) moving the photomask blank to move the defect on the photomask blank surface to a position observable by an inspection optical system, irradiating inspection light to a defect-bearing surface region, and collecting the reflected light from the irradiated region as a magnified image of the region via the inspection optical system,
   (A3) extracting a feature parameter from the magnified image, and
   (A4) identifying the shape of the defect on the basis of the feature parameter combined with the structure of the photomask blank thin film, wherein
   the magnified image in step (A2) is created by diffraction components of the reflected light that are transmitted through the inspection optical system, and higher-order diffraction components as said diffraction components are asymmetric between positive and negative sides with respect to the zeroth-order diffraction component (specular component) of the reflected light.

2. The method of claim 1 wherein step (A3) includes a processing step of comparing a variation of the light intensity level of a defect area in the magnified image with the light intensity level of a defect-surrounding area, for thereby extracting the feature parameter from the defect inspection image which contains the intensity difference between a bright part with a high light intensity and a dark part with a low light intensity and the positional arrangement relationship between the bright part and the dark part.

3. The method of claim 1 wherein in step (A4), the shape of the defect is identified on the basis of data including the feature parameter of the magnified image and the structure of the photomask blank thin film, and with reference to a table which is previously formed based on optical simulation or empirical data for enabling a choice between pinhole defect and bump defect.

4. The method of claim 3 wherein provided that the outermost surface of the photomask blank under inspection is a thin film which is transparent to the inspection light, when a feature parameter indicating that the magnified image of the defect is a bright part-predominant image is extracted in step (A3), the defect detected is identified to be a pinhole defect.

5. The method of claim 3 wherein provided that the photomask blank under inspection has a film structure that a thin film at the outermost surface has a higher reflectivity of inspection light than an underlying layer, when a feature parameter indicating that the magnified image of the defect is a dark part-predominant image is extracted in step (A3), the defect detected is identified to be a pinhole defect.

6. The method of claim 1 wherein the thin film has a thickness of up to 10 nm.

7. The method of claim 1 wherein the inspection light is light having a wavelength of 210 to 550 nm.

8. A system for inspecting a defect on a photomask blank having at least one thin film on an optically transparent substrate, comprising
an inspection system adapted to irradiate inspection light to a surface region of the thin film and to capture the reflected light from the irradiated region, for thereby inspecting any defects on the surface of the photomask blank, and
a computer having installed therein a program for executing the steps in the photomask blank defect inspection method of claim 1.

9. A method of sorting photomask blanks, comprising sorting photomask blanks having no pinhole defects, based on the identification whether defects are of bump or pit shape by the inspection method of claim 1.

10. A method for manufacturing a photomask blank, comprising the steps of:
forming at least one thin film on an optically transparent substrate to construct a photomask blank, and
sorting a photomask blank having no pinhole defects by the sorting method of claim 9.

11. A method for inspecting a defect on a photomask blank, comprising the steps of:
(A1) preparing a photomask blank having at least one thin film on an optically transparent substrate, the photomask blank bearing a defect on its surface,
(A2) moving the photomask blank to move the defect on the photomask blank surface to a position observable by an inspection optical system, irradiating inspection light to a defect-bearing surface region, and collecting the reflected light from the irradiated region as a magnified image of the region via the inspection optical system,
(A3) extracting a feature parameter from the magnified image, and (A4) identifying the shape of the defect on the basis of the feature parameter combined with the structure of the photomask blank thin film, wherein in step (A4), the shape of the defect is identified on the basis of data including the feature parameter of the magnified image and the structure of the photomask blank thin film, and with reference to a table which is previously formed based on optical simulation or empirical data for enabling a choice between pinhole defect and bump defect, and wherein
i) provided that the outermost surface of the photomask blank under inspection is a thin film which is transparent to the inspection light, when a feature parameter indicating that the magnified image of the defect is a bright part-predominant image is extracted in step (A3), the defect detected is identified to be a pinhole defect, or
ii) provided that the photomask blank under inspection has a film structure that a thin film at the outermost surface has a higher reflectivity of inspection light than an underlying layer, when a feature parameter indicating that the magnified image of the defect is a dark part-predominant image is extracted in step (A3), the defect detected is identified to be a pinhole defect.

12. The method of claim 11 wherein the magnified image in step (A2) is created by diffraction components of the reflected light that are transmitted through the inspection optical system, and higher-order diffraction components as said diffraction components are asymmetric between positive and negative sides with respect to the zeroth-order diffraction component (specular component) of the reflected light.

13. The method of claim 11 wherein step (A3) includes a processing step of comparing a variation of the light intensity level of a defect area in the magnified image with the light intensity level of a defect-surrounding area, for thereby extracting the feature parameter from the defect inspection image which contains the intensity difference between a bright part with a high light intensity and a dark part with a low light intensity and the positional arrangement relationship between the bright part and the dark part.

14. The method of claim 11 wherein the thin film has a thickness of up to 10 nm.

15. The method of claim 11 wherein the inspection light is light having a wavelength of 210 to 550 nm.

16. A system for inspecting a defect on a photomask blank having at least one thin film on an optically transparent substrate, comprising
an inspection system adapted to irradiate inspection light to a surface region of the thin film and to capture the reflected light from the irradiated region, for thereby inspecting any defects on the surface of the photomask blank, and
a computer having installed therein a program for executing the steps in the photomask blank detect inspection method of claim 11.

17. A method of sorting photomask blanks, comprising sorting photomask blanks having no pinhole defects, based on the identification whether defects are of bump or pit shape by the inspection method of claim 11.

18. A method for manufacturing a photomask blank, comprising the steps of:
forming at least one thin film on an optically transparent substrate to construct a photomask blank, and sorting a photomask blank having no pinhole defects by the sorting method of claim 17.

* * * * *